(12) United States Patent
Escal

(10) Patent No.: US 7,025,714 B2
(45) Date of Patent: Apr. 11, 2006

(54) PROCESS TO BALANCE A ROTATABLE PLATE OF A CENTRIFUGE AND CENTRIFUGE USING THE PROCESS

(75) Inventor: Philippe Escal, Castelnau le Nez (FR)

(73) Assignee: Diagyr, Jacou (FR)

(*) Notice: Subject to any disclaimer, the term of this patent is extended or adjusted under 35 U.S.C. 154(b) by 35 days.

(21) Appl. No.: 10/901,083

(22) Filed: Jul. 29, 2004

(65) Prior Publication Data

US 2005/0026765 A1 Feb. 3, 2005

(30) Foreign Application Priority Data

Jul. 29, 2003 (FR) .................................. 03 09281

(51) Int. Cl.
 *B04B 9/14* (2006.01)
 *B04B 13/00* (2006.01)
(52) U.S. Cl. .............................. 494/1; 494/10; 494/20; 494/82; 74/572.4
(58) Field of Classification Search .................... 494/1, 494/10, 12, 20, 23, 27, 29, 33, 82, 84; 422/72; 210/85, 144; 68/23.1, 23.2; 73/457, 458; 74/573 R, 573 F, 572.4
 See application file for complete search history.

(56) References Cited

U.S. PATENT DOCUMENTS

| 3,692,236 | A | * | 9/1972 | Livshitz et al. ............... 494/20 |
| 3,921,898 | A | * | 11/1975 | Finkel ........................ 74/572.4 |
| 4,157,781 | A | * | 6/1979 | Maruyama ................... 494/20 |
| 4,295,386 | A | * | 10/1981 | Zhivotov ..................... 464/180 |
| 4,513,464 | A |   | 4/1985 | Rettich et al. |
| 4,919,646 | A | * | 4/1990 | Perdriat ........................ 494/1 |
| 5,715,731 | A | * | 2/1998 | Koch ........................ 74/572.4 |
| 5,800,331 | A |   | 9/1998 | Song |
| 5,921,148 | A | * | 7/1999 | Howell ..................... 74/572.4 |
| 6,945,129 | B1 | * | 9/2005 | Escal .......................... 422/72 |
| 6,949,063 | B1 | * | 9/2005 | Baik et al. .................... 494/82 |
| 2005/0026765 | A1 | * | 2/2005 | Escal .......................... 494/20 |

FOREIGN PATENT DOCUMENTS

| DE | 100 17 904 |   | 10/2001 |
| FR | 2 776 773 |   | 10/1999 |
| GB | 2359772 A | * | 9/2005 |
| JP | 63-62563 | * | 3/1988 |
| JP | 2003-236409 | * | 8/2005 |
| WO | 00/29122 | * | 5/2000 |

* cited by examiner

Primary Examiner—Charles E. Cooley
(74) Attorney, Agent, or Firm—Young & Thompson

(57) ABSTRACT

Centrifuge includes a plate, a detector for the position of the plate, a monitoring and control unit, to turn the plate and to stop it in predetermined angular positions; characterized by several balancing containers, a centrifugal detector, a device for providing a balancing product located at a fixed station, calculating means adapted to determine an angular position ($\theta_B$) and a mass ($m_0$) of an unbalance (B) as well as an angular position ($\theta_E$) for a balancing mass ($m_1$). The monitoring and control unit control the stopping of the plate in a predetermined angular position for the balancing mass ($m_1$) in correspondence with the fixed station, and to control said device for supplying a balancing product to fill the one of the balancing containers that is located at the fixed station.

12 Claims, 7 Drawing Sheets

PROCESS TO BALANCE A ROTATABLE PLATE OF A CENTRIFUGE AND CENTRIFUGE USING THE PROCESS

The present invention relates to a process for balancing a rotatable plate of a centrifuge comprising a position detector adapted to supply a signal indicative of an angular position of the rotatable plate, and several tube carriers which are located in predetermined angular positions on the periphery of the rotatable plate and which each have means adapted to receive a specimen tube.

Certain dosages, carried out for example by medical analysis laboratories, require preliminary separation by gravitation into several phases of different densities, of a liquid specimen to be analyzed. To accelerate the separation process, there is used a centrifuge which permits increasing considerably the force of gravity, by means of centrifugal acceleration. However, the plate of a centrifuge must be balanced as best possible before its rotation, to avoid unbalance disturbing the movement, giving rise to a high level of vibrations or even leading to mechanical damage.

At present, the balancing of the rotatable plate of the rotor of the centrifuge takes place by distributing as best possible, manually, the mass of the specimens to be treated. For example, as described in EP-A-0 088 440, during loading of the specimen tubes into the tube carriers, a control unit of the centrifuge causes the rotor to turn stepwise so as sequentially to bring the tube carriers below a loading opening in a predetermined order. More precisely, the first specimen tube is placed in a first tube carrier, a second tube for the specimen is then placed in a second tube carrier diametrically opposed to the first tube carrier, a third tube with a specimen is then placed in a third tube carrier, a fourth tube with a specimen is then placed in a fourth tube carrier diametrically opposed to the third tube carrier, and so on. Such a balancing process can give a good result only if an even number of specimen tubes is disposed in the tube carrier of the rotor, and also under the condition that the specimen tubes that are diametrically opposed on the rotor and their contents each have the same weight, which is rarely the case in practice.

In other known system (WO-A-98/01760), each tube carrier is constituted by a sort of basket comprising several recesses, each recess being adapted to receive a specimen tube containing a specimen to be centrifuged and to be analyzed, or if desired to receive a dummy test tube, containing a predetermined balancing mass. There is provided an even number of baskets, for example four baskets, which are grouped pair-wise, the two baskets of each pair being adapted to be installed in diametrically opposed positions on the rotor of the centrifuge. The specimen tubes and the baskets are weighed, and the positions of the specimen tubes and the baskets are correlated with their weight so as to obtain a symmetrical distribution in each basket. More precisely, the baskets loaded with specimen tubes are balanced for example by loading each time a pair of baskets by using a symmetrical distribution of load in the baskets, which contain equal numbers of loaded cases of a specimen tube, and/or by placing dummy test tubes in the baskets which require supplemental weight to obtain balancing. The dummy test tubes are selected from a supply of dummy test tubes containing predetermined balancing masses, whose weights have graduated values. The dummy test tubes are added into the baskets which require a supplemental weight such that the weight difference between the two baskets of a basket pair will not exceed 10 grams.

Although this known system of operations of loading can be carried out by means of a robot arm controlled by a computer, the loading operations are relatively long and complicated. Moreover, such a known process for loading cannot be used in the case of relatively simple centrifuges which do not comprise baskets, but a single tube carrier, hence a single specimen tube in each angular position at the periphery of the rotor. Finally, given the tolerance of 10 grams for the weight difference per pair of baskets, when there are four baskets, there can be in the most unfavorable case a total unbalance of about 14 grams. However, the nominal speed of rotation in the course of centrifugation can reach 3,600 rpm, namely, for a radius of gyration of 0.2 meter, a centrifugal acceleration which can reach about 28,400 m·s$^{-2}$ or 2,900 g (g=9.81 m·s$^{-2}$). For an unbalance of 14 grams, this leads to a centrifugal force of about 400 N, which is relatively great force.

The present invention thus has for its object to propose a process to carry out automatic balancing of the rotatable plate or rotor of a centrifuge of the type defined in the preamble, which process permits obtaining much higher precision of balancing.

To this end, the process according to the invention is characterized in that it comprises the steps consisting:

a) in using as a tube carrier, tube carriers each having a balancing container in addition to said means adapted to receive a specimen tube;

b) in loading at least a certain number of said tube carriers each with a specimen tube filled with a specimen of liquid to be centrifuged;

c) in turning the rotatable plate at a predetermined speed of rotation;

d) in determining, based on said predetermined speed of rotation and on the basis of the signal supplied by the position detector and a signal supplied by an acceleration detector of the rotatable plate, an angular position and an unbalance mass on the rotatable plate, due to unequal loading of said rotatable plate;

e) in determining, based on the angular position of the unbalance determined in step d), at least one angular position on the rotatable plate for at least one balancing weight;

f) in reducing the speed of the rotating plate and bringing it by one slow rotation to a stop position such that the angular position determined in step e) is located in correspondence with a fixed station for supplying a balancing product; and g) in filling the balancing container which is located at the fixed supply station when the rotatable plate is in said stopped position, with a quantity of balancing product having a mass equal to at least a fraction of the unbalancing mass determined in step d).

The process of the invention can moreover have one or another of the following characteristics.

In a first embodiment of the process, step e) consists:

e1) in computing the angular position which is diametrically opposed, on the rotatable plate, to the angular position of the unbalance determined in step d);

e2) in verifying whether the angular position calculated in step e1) corresponds to one of said defined angular positions of the tube carrier and of the balancing container associated therewith and, in the affirmative, in adopting as the angular position for the balancing weight mass, the angular position calculated in step e1), and if not, in adopting as the angular position for the balancing mass the angular position of the tube carrier and of the balancing container associated therewith which is nearest the angular position calculated in step e1).

In a second embodiment of the process, step e) consists:

e1) in computing the angular position which is diametrically opposite, on the rotating plate, to the angular position of the unbalance determined in step d);

e2) in verifying whether the angular position calculated in step e1) corresponds to one of said defined angular positions of the tube carrier and of the balancing container associated therewith and, in the affirmative, in adopting as the angular position for the balancing mass the angular position calculated in step e1), and if not, in adopting as angular positions for at least two balancing masses at least two angular positions corresponding to at least two of the tube carriers and to the balancing containers associated therewith which are located on opposite sides of the angular position calculated in step e1), and in calculating at least two balancing masses to be placed respectively in the balancing containers corresponding to the adopted angular positions, said calculated balancing masses corresponding to fractions of the unbalance mass determined in step d) such that the vectorial sum of the centrifugal forces due to the calculated balancing masses once placed in the balancing containers located in said adopted angular positions, balances the centrifugal force due to the unbalance mass.

The invention also has for its object centrifuges permitting the practice of the process according to the invention.

To this end, the invention provides a centrifuge comprising:

a) a frame;

b) a plate rotatably mounted on the frame and having several tube carriers located in defined angular positions about the periphery of the rotatable plate, each tube carrier being adapted to receive a specimen tube;

c) guide means to cause the rotatable plate to turn;

d) a position detector adapted to provide a signal indicative of an angular position of the rotatable plate;

e) a monitoring and control unit receiving said signal indicative of the angular position and adapted to control said drive means so as to cause the rotatable plate to turn at least at a predetermined speed of rotation and to stop said rotatable plate in predetermined angular positions;

characterized by f) several balancing containers which are respectively joined to the tube carrier on the rotatable plate;

g) an acceleration detector adapted to supply a signal indicative of the value of centrifugal acceleration to which the rotatable plate is subject when it turns at a predetermined speed;

h) a device for supplying a balancing product located on the frame at a station adjacent the periphery of the rotatable plate;

i) calculating means included in the monitoring and control unit, adapted to determine, on the basis of said predetermined speed of rotation and on the basis of signals provided by the position detector and the acceleration detector, an angular position and an unbalance mass on the rotatable plate, due to unequal loading of said rotatable plate;

j) said calculating means being adapted to determine, on the basis of the determined angular position of the unbalance, at least one angular position on the rotatable plate for at least one balancing mass;

k) said monitoring and control unit being adapted to control said drive means such that they bring the rotatable plate to a stopped position such that the determined angular position for the balancing weight will be located in correspondence with said fixed station, and in controlling said supply device for balancing product to fill the one of the balancing containers which is located in the fixed station when the rotatable plate is in said stopped position, with a quantity of balancing product having a mass equal to at least a fraction of the unbalance mass determined by the calculating means.

The centrifuge of the invention can moreover have one or several of the following characteristics:

said rotatable plate, said position detector, said acceleration detector and said drive means are carried by a movable support which is mounted pivotably relative to the frame about a vertical pivotal axis parallel to the axis of rotation of the rotatable plate and which is adapted to oscillate on opposite sides of a neutral position when the rotatable plate turns at said predetermined speed with an unequal load;

the axis of rotation of the rotatable plate is located at a first distance from the vertical pivotal axis, and the acceleration detector is located at a second distance from said axis of vertical pivoting in a vertical plane defined by said vertical pivoting axis and by said axis of rotation, said second distance being greater than said first distance;

said calculating means calculate the mass $m_0$ of the unbalance according to a first formula:

$$m_0 = \frac{\Gamma'_0}{\gamma_c} \cdot \frac{M}{K}$$

in which $\Gamma'_0$ is an acceleration value measured by the acceleration detector, K is a coefficient of amplification whose value is equal to the ratio (L2/L1) of said second and first distances, M is the total mass of the movable support and of all the pieces of the centrifuge carried by said movable support; and $\gamma_c$ is the value of centrifugal acceleration due to the mass $m_0$ of the unbalance when the rotatable plate turns at the predetermined speed of rotation;

the calculating means recalculate the mass $m_0$ of the unbalance according to a second formula:

$$m_0 = \frac{m_1}{K} \cdot \frac{\Gamma'_0}{\gamma_c} \cdot \frac{\Gamma'_1 + K\gamma_c}{\Gamma'_0 - \Gamma'_1}$$

in which $m_1$ is a first balancing mass calculated according to the first formula and $\Gamma'_1$ is a value of acceleration measured by the acceleration detector when the rotatable plate provided with the first balancing mass is driven in rotation at the predetermined speed of rotation, and the calculating means then calculate a second balancing mass $m_2 = m_0 - m_1$, from the second formula so as to complete the balancing of the rotatable plate;

the centrifuge comprises this engageable indexing means which are controlled by the monitoring and control unit so as to maintain said movable support in said neutral position when the rotatable plate is stopped and when it turns at a speed substantially slower than said predetermined speed of rotation;

the balancing product is a liquid;

the supply device for balancing product comprises:

a) at the fixed station, a vertical hollow filling and emptying needle and a rising and lowering mechanism, controlled by the monitoring and control unit, to move said needle vertically between an upper ready position, in which the lower end of the needle is at a higher level than an upper opening of the balancing container to be filled, and at least one lower filling/emptying position in which the needle is engaged in said balancing container to be filled or emptied;

b) a reservoir of balancing liquid; and c) a pump connected to said reservoir of balancing liquid and to said needle by flexible tubes and by an electrovalve controlled by the monitoring and control unit, said electrovalve having a neutral ready position, a working position in which the balancing liquid can circulate from the reservoir toward the needle, and a second working position in which the balancing liquid can circulate from the needle toward the reservoir;

the centrifuge moreover comprises a detector for the liquid level arranged to detect a liquid level in the balancing container located at said fixed station and to supply a signal indicative of the detected liquid level usable by the monitoring and control unit to control the pump and/or the electrovalve.

Other characteristics and advantages of the invention will become apparent from the following description of an embodiment given by way of example, with reference to the accompanying drawings, in which.

Figure 1:
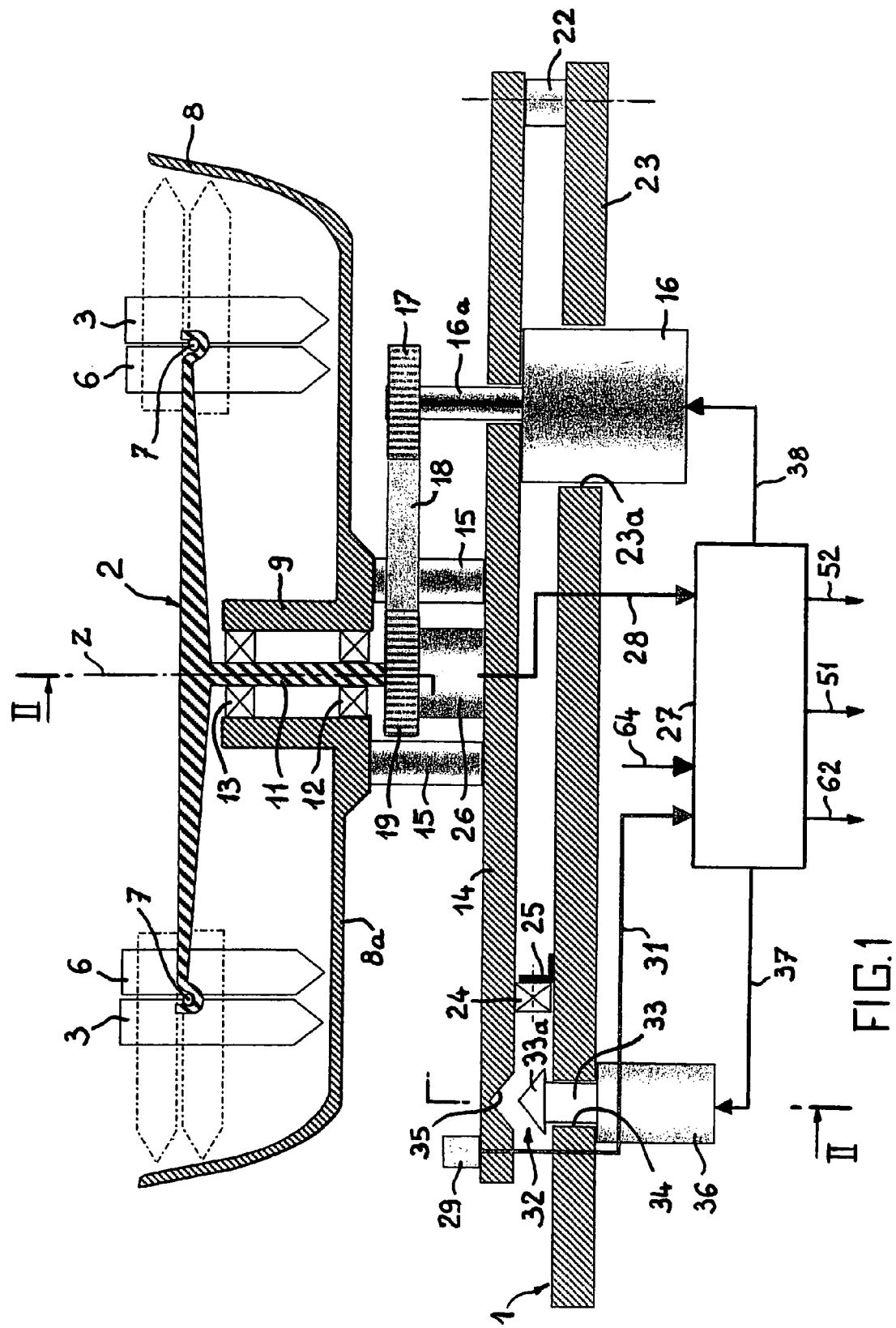
FIG. 1 is a schematical cross-sectional view of a centrifuge according to the invention.
Figure 2:
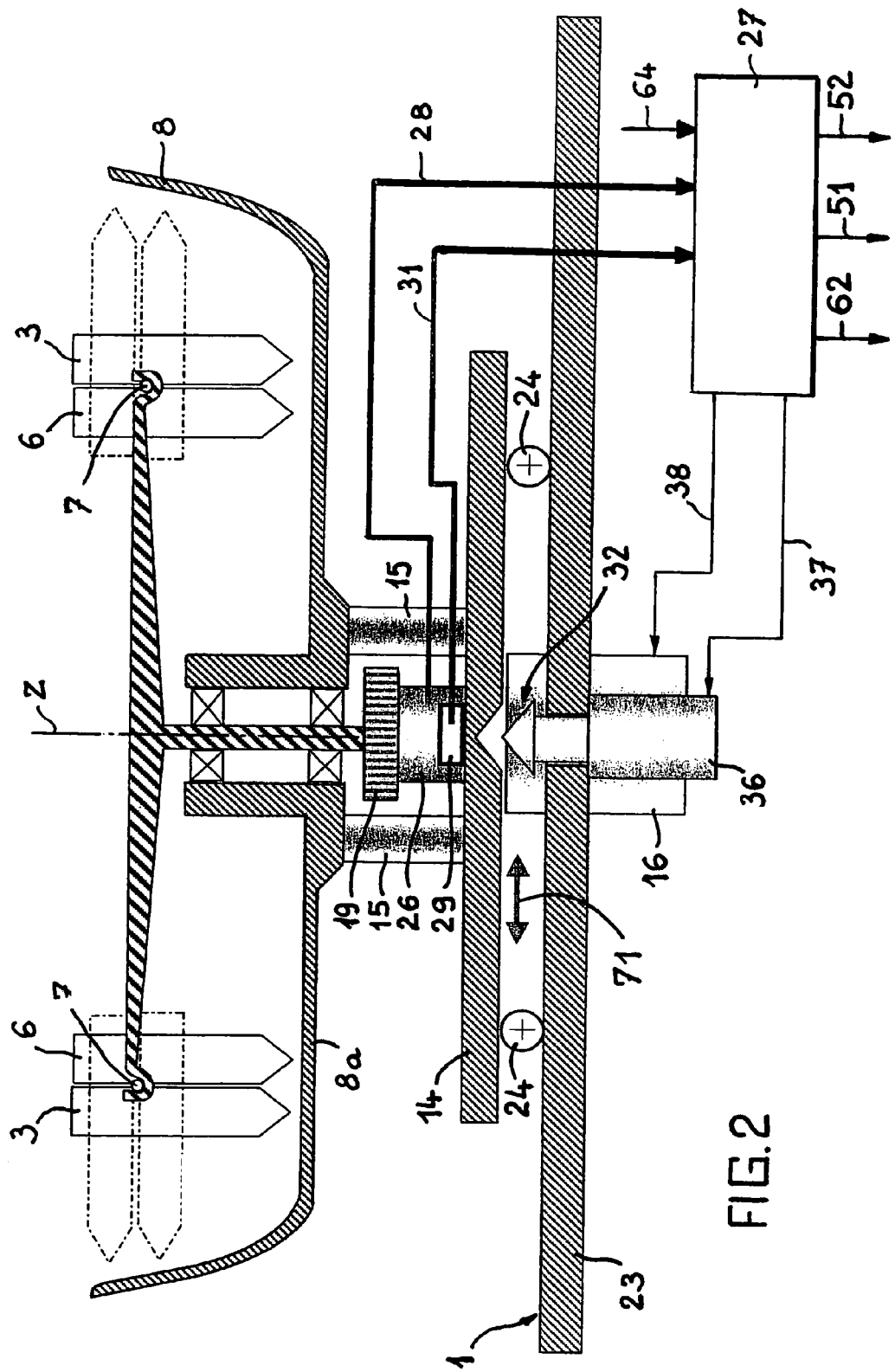
FIG. 2 is a vertical cross-sectional view on the line II—II of FIG. 1.

Referring to FIGS. 1 and 2, it can be seen that the centrifuge according to the invention comprises a frame 1 on which is mounted a rotatable plate 2 having several tube carriers 3 located in predetermine angular positions about the periphery of the rotatable plate 2. Preferably, the tube carriers 3 are regularly distributed at the periphery of the rotatable plate 2. Each tube carrier is adapted to receive a specimen tube 4 closed by a plug 5 and containing a specimen that is to be separated into several phases by centrifugation.

With each tube carrier 4 is associated a balancing container 6. Each tube carrier 4 and the balancing container 6 which is connected to it forms an assembly which is swingably bonded relative to the rotatable plate 2 so as to be able to swing about a horizontal swinging axis 7 which extends tangentially to the circumference of the rotatable plate 2. Thus, each assembly constituted by a tube carrier 3 and by the balancing container 6 which is joined to it can swing between a vertical rest position shown in full line in FIGS. 1 and 2, when the plate 2 does not turn, and the horizontal or substantially horizontal centrifugation position shown in broken lines in FIGS. 1 and 2, when the rotatable plate 2 is driven in rotation at high speed, for example 3,000 rpm or more.

The plate is disposed in a basin 8 with a circular edge, whose diameter is substantially greater than that of the plate 2. At the middle of the basin 8 is located a cylindrical well 9, which projects upwardly from the bottom 8a of the basin 8. The plate 2 is fixed to the upper end of a vertical shaft 11 which extends downwardly within the well 9 and is rotatably mounted by means of roller bearings 12 and 13. The plate 2 and the shaft 11 can be made of a single piece, preferably of a light material, for example of a plastic material or of light metal such as aluminum or aluminum alloy. The basin 8 is supported by a horizontal support plate 14 by means of several column-crosspieces, so as to provide a space between the plate 14 and the bottom of the basin 8. The lower end of shaft 11 projects into the above-mentioned space. The shaft 11 and accordingly the plate can be driven in rotation by an electric motor 16, preferably a stepping motor, which is fixed to the plate (14) below the latter. The output shaft 16a of the motor 16 passes through the plate 14 and carries at its upper end a toothed pulley 17 kinematically connected by a toothed belt 18 to another toothed pulley 19 which is fixed to the lower end of the shaft 11.

As constructed, the assembly constituted by the plate 2, the tube carrier 3, the balancing container 6 and the shaft 11 is a balanced assembly. However, in service, if the plate is not loaded uniformly, the rotatable plate 2 will thus be unbalanced. Such a situation can take place particularly if all the tube carriers 3 are not provided with a specimen tube and if, in this case, the tubes with specimens are not uniformly distributed in the tube carriers 3 and/or if the specimens contained in all the specimen tubes or at least all those which are contained in specimen tubes located in the tube carriers occupying diametrically opposed positions on the rotatable plate, do not have the same weight, which can happen frequently in practice. Thus, in these cases, the vectorial sum of the elemental centrifugal forces applied at each point on the plate 2 is not zero and, as is well known, the plate 2 is thus subjected to a resulting centrifugal force $F_c$ (FIG. 5) which is directed radially relative to the plate 2 and which is transmitted to the support of the latter, in this case the plate 14, by means of two bearings 12 and 13, of the well 9 and the basin 8 and of the columns-crosspieces 15. This resulting centrifugal force $F_c$ is applied at a single point B (FIG. 5) on the plate 2, called the unbalance, which turns with the plate 2, but whose position on said plate depends on the distribution of the loads on the latter and can thus vary from one loading to the next. As is well known, the force $F_c$ applied to the unbalance B disturbs the movement of the plate 2, giving rise to vibrations and can lead to mechanical damage, particularly to the bearings 12 and 13. To avoid this, it is necessary to compensate the force $F_c$ by a balancing force $F_e$ (FIG. 5) having an equal intensity and opposite direction to the intensity of the direction of the force $F_c$.

To this end, in the centrifuge of the invention, a balancing container 6 is added to each tube carrier 3, a means are provided to determine the angular position and the mass of the unbalance B and thereby to determine the angular position of the point E which is diametrically opposite the unbalance B and to which must be added a balancing weight to obtain the compensating centrifugal force $F_c$ balancing the centrifugal force $F_e$ applied to the unbalance B. There is moreover provided a device 21 for supplying balancing product, which is located on the frame 1 of the centrifuge at a fixed station adjacent the periphery of the rotating plate 2, as well as means permitting automatically bringing the determined point E of the rotating plate 2 to the supply device 21 so as to fill the balancing containers 6 corresponding to the point E with a suitable mass of balancing product, for example of water as will now be described with respect to an embodiment of the present invention.

Figure 3:
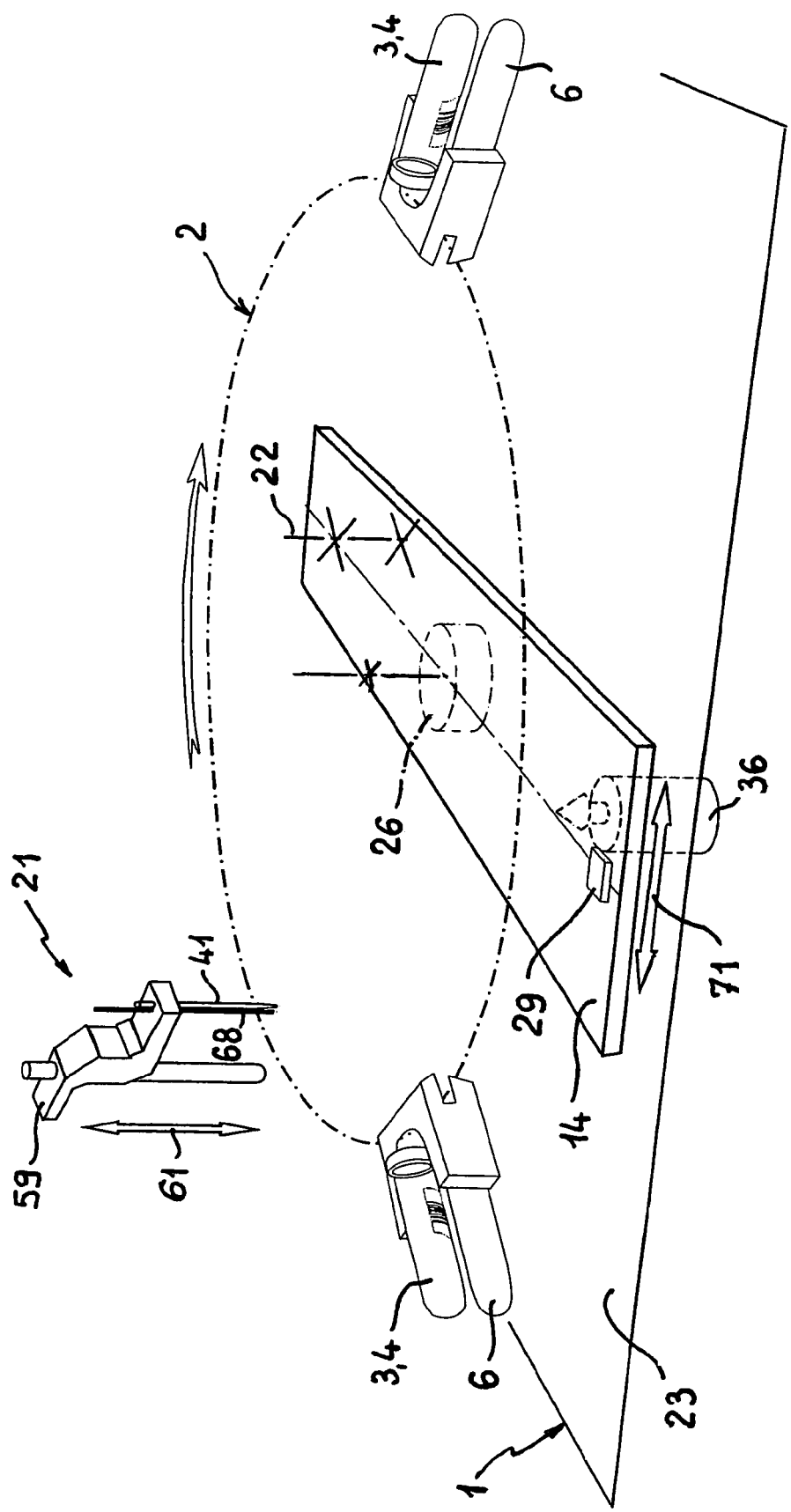
FIG. 3 is a schematic perspective view showing the operation of the centrifuge of FIGS. 1 and 2.

As shown in FIGS. 1 to 3, the support plate 14 has an elongated rectangular shape and is pivotally mounted, at one of its ends, on a vertical axle 22 carried by a horizontal plate 23 which forms part of the frame 1. At its opposite end, the support plate 14 bears on the plate 23 by means of at least one roller, preferably two rollers 24 mounted on roller bearings or needle bearings. Each roller 24 is carried by one of the legs of an angle arm 25 whose other leg is fixed to the upper surface of the plate 23, as shown in FIG. 1. In this case, the support plate 14 rests on the rollers 24. As a modification, the angle arms 25 could be fixed to the lower surface of the support plate 14 and, in this case, the rollers could roll on the upper surface of the plate 23.

The support plate 14 carries a position detector 26, comprising a rotor (not shown) which is connected to the lower end of the shaft 11 of the plate 2 so as to turn with the latter. As will be explained in detail later, the position detector 26 is adapted to supply a signal indicative of an angular position of the rotatable plate 2 to a monitoring and control unit 27 of the centrifuge via a line 28. The support plate 14 also carries an acceleration detector 29 which is connected by a line 31 to the control and monitoring unit 27 and which is adapted to supply to the latter a signal indicative of the value of acceleration to which the support plate 14 and all the elements carried by the latter are subject by reason of the presence of an unbalance on the rotatable plate 2, when the latter is driven in rotation at a predetermined speed of rotation. As is seen particularly in FIG. 5, the acceleration detector 29 is preferably disposed at a distance L2 from the axle 22 greater than the distance L1 from the center O of the plate 2 to the axle 22.

The support plate 14 can be held in a predetermined rest position or neutral position by indexing means 32. The indexing means 32 can comprise for example a vertical peg 33, which can slide in a hole 34 of the plate 23 and which comprises, at its upper end, a conical head 33a that can be engaged in a conical impression 35 formed in the lower surface of the support plate 14. A spring (not shown) urges the peg 33 so as to maintain its head 33a in the conical imprint 35. An electromagnet 36, whose movable armature is connected to or forms an integral part of the peg 33, permits, when it is excited, to cause the head 33a of the peg 33 to leave the impression 35, to permit the support plate 14 to pivot freely about the axle 22. The electromagnetic 36 is connected by a control line 37 to the monitoring and control unit 27. Another control line 38 connects the monitoring and control unit 27 to the motor 16.

Figure 4:
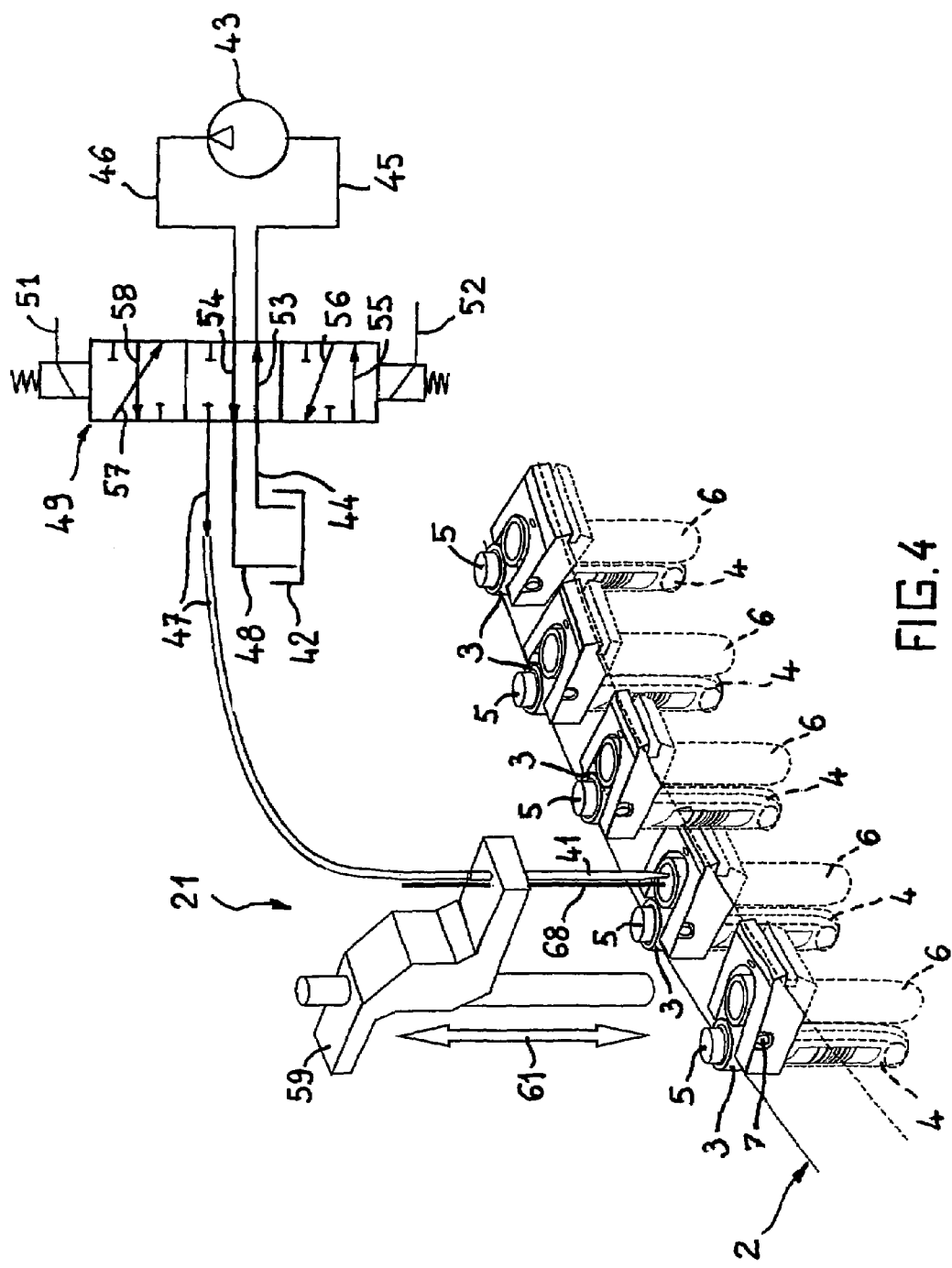
FIG. 4 is a fragmentary view of the centrifuge of FIGS. 1 to 3, showing how to carry out the filling of a balancing container of the rotatable plate of the centrifuge.

In the case in which a liquid is used, for example water, as the balancing product to fill one or several balancing containers 6, the supply device 21 for balancing product can comprise, as shown in FIG. 4, a vertical hollow filling emptying needle 41, a reservoir 42 for balancing liquid, and a pump 43 connected to the reservoir 42 and the needle 41 by flexible tubes 44–48 and by an electrovalve 49 controlled by the monitoring and control unit 27 by control lines 51 and 52.

The electrovalve 49 has three positions, namely:

a neutral ready position (shown in FIG. 4) in which the pump 43 sucks balancing liquid from the reservoir 42 through the tube 44, the passage 53 of the side of the electrovalve and the tube 45, and moves the balancing liquid toward the reservoir 42 through the valve 46, the passage 54 of the slide of the electrovalve and the tube 48;

a first working or filling position, in which the slide of the electrovalve is also upwardly relative to the position shown in FIG. 4, and in which the filling liquid can circulate from the reservoir 42 toward the needle 41 through the valve 44, the passage 55 of the electrovalve slide, the tube 45, the pump 43, the tube 46, the passage 56 of the slide of the electrovalve and the tube 47;

a second working position or emptying position, in which the slide of the electrovalve is offset downwardly relative to the position shown in FIG. 4, and in which the filling liquid can circulate from the needle 41 toward the reservoir 42 through the tube 47, the passage 57 of the electrovalve slide, the tube 45, the pump 43, the tube 46, the passage 58 of the slide of the electrovalve and the tube 44.

The needle 41 is carried by a support 59 which can be moved vertically by raising and lowering mechanism, indicated symbolically by the double arrow 61, which is controlled by the monitoring and control unit 27 through a control line 62. The mechanism 61 can move the needle 41 between an upper ready position, in which the lower end of the needle 41 is at a higher level than an upper opening of the balancing container (6) to be filled, to permit the plate 2 to turn without striking the needle 41, and at least one lower filling/emptying position in which said needle 41 is engaged in the balancing container 6 to be filled or emptied.

The centrifuge moreover comprises a liquid level detector 63 (FIG. 10) connected by a line 64 to the monitoring and control unit 27. The level detector 63 is arranged to detect a liquid level in a balancing container 6 located in correspondence with the supply device 21 and to provide to the monitoring and control unit 27 a signal indicative of the detected level of liquid usable by said unit 27 to control the pump 43 and/or the electrovalve 49.

Figure 10:
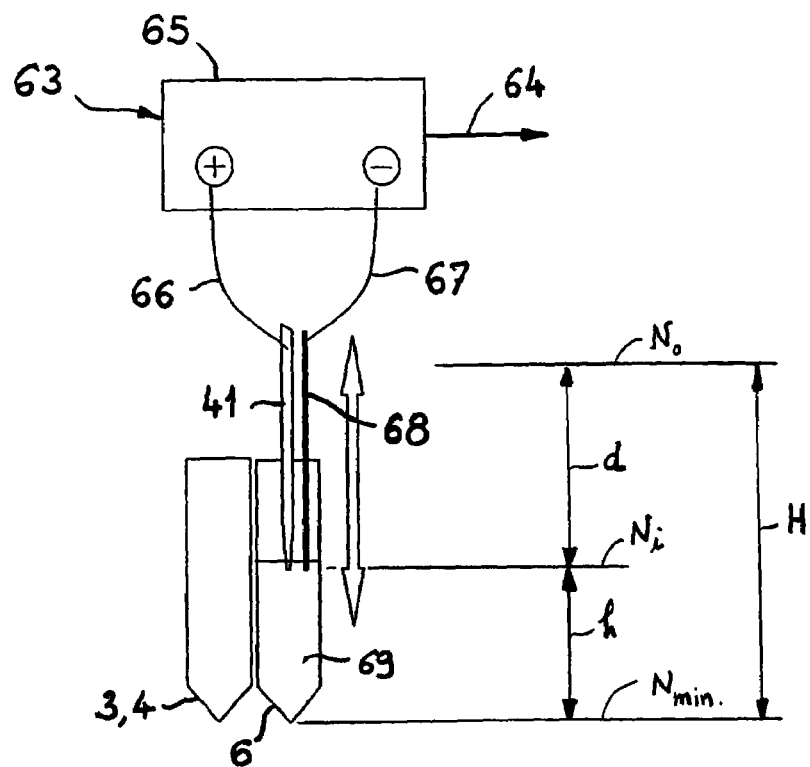
FIG. 10 is a fragmentary schematic view showing the means permitting determining a liquid level in a balancing container.

As shown in FIG. 10, the level detector 63 can include a source of continuous voltage 65 connected by wires 66 and 67 respectively to the needle 41, which can be of conductive metal, and an electrode 68 which is carried by the support 59 and which extends parallel to the needle 41. As is shown in FIGS. 3 and 4, the needle 41 and the electrode 68 extend vertically downwardly from the support 59 by the same distance, such that their lower ends are located at a same level, this level itself depending on the position given to the support 59 by the raising and lowering mechanism 61. The needle 41 and the electrode 68 are electrically insulated from each other such that normally no current flows in the wires 66 and 67. On the other hand, when a conductive liquid, for example water, contained in a balancing container 6 comes into contact with the lower ends of the needle 41 and the electrode 68, a conductive path is established and a current thus flows through the wires 66 and 67. This current can be used to produce in the line 64 a signal indicating that the liquid contained in the balancing container 6 has reached a predetermined level corresponding to the level of the lower ends of the needle 41 and the electrode 68.

Given that, by their construction, all the balancing containers 6 are identical and are fixed in the same manner to the plate 2, all the containers 6 thus have the same internal diameter and their external diameter is located at a level $N_{min}$ which is well defined and known, below the level $N_0$ (FIG. 10), itself well defined and known, at which are located the lower ends of the needle 41 and the electrode 68 when the support 59 is in the upper ready position mentioned above. On the other hand, when the support 59 is moved vertically by the mechanism 61, there can easily be known at any time the vertical distance d at which the lower ends of the needle 41 and the electrode 68 are located relative to the level $N_0$. For example, if the mechanism 61 comprises a ball screw having a pitch p that is predefined and driven in rotation by a stepping motor associated with an angular coder adapted to supply a signal indicating the number of turns made by the ball screw from a starting position corresponding to the upper ready position of the support 59, calculating means provided in the monitoring and control unit 27 can then easily compute the distance d which would be equal to the product of the pitch P times the number of turns made by the screw. Knowing the vertical distance H between the level $N_0$ and $N_{min}$ and knowing the vertical distance d, it is possible to calculate by their difference, the vertical distance h between the level $N_{min}$ and the level $N_i$ in which are located the lower ends of the needle 41 and the electrode 68.

As a result, if the balancing container 6 is filled to the level $N_i$, knowing the vertical distance h, the internal diameter of the balancing container 6 and the density of the liquid 69, for example water, contained in the balancing container 6, it is possible to know the volume and the weight of the liquid in the balancing container 6.

Conversely, if it is desired to fill the balancing container 6 with a desired weight of balancing liquid, the calculating means included in the monitoring and control unit 27 can calculate the height h corresponding to the desired weight of balancing liquid and, by their difference with the vertical distance H, thereby find the vertical distance d to which the support 29 must descend from its upper ready position, corresponding to the level $N_0$, to bring the lower ends of the needle 41 and the electrode 68 to the level $N_i$ corresponding to the vertical distance d that is calculated. After the lower ends of the needle 41 and the electrode 68 have been disposed at level $N_i$, the monitoring and control unit 27 can control the filling of the balancing container 6 by actuating the electrovalve 49 so as to place it in its first working position (filling position). When the liquid introduced into the balancing container 6 reaches the level $N_i$, the level detector 63 emits over the line 64 a signal which is used by the monitoring and control unit 27 to return the electrovalve 49 to its neutral ready position in which no liquid is sent to the needle 41.

Figure 5:
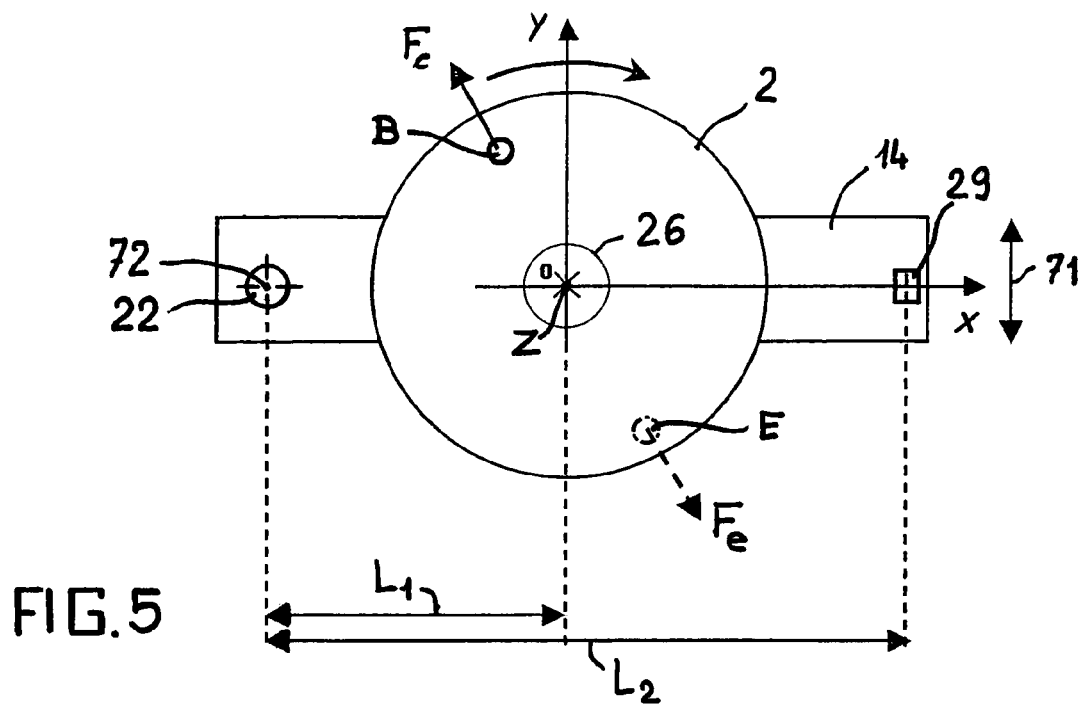
FIG. 5 is a schematic plan view permitting explaining the principle on which is based the process of the invention to determine the angular position of an unbalance on the rotating plate and the mass of said unbalance.

When it is desired to balance the rotating plate 2 before a centrifugation operation, there are first of all placed the specimen tubes, each containing a specimen of liquid to be centrifuged, into at least a certain number of tube carriers 3 on the rotating plate 2. This loading operation of the plate 2 can be carried out manually or with the help of a robot arm, and it is preferably carried out, but not necessarily, by distributing the specimen tubes as regularly as possible into the tube carriers 3 at the periphery of the plate 2. For example, the specimen tubes can be placed two by two in the tube carriers located in diametrically opposed positions at the periphery of plate 2. During this operation, the indexing means 32 are active and hold the support plate 14 in a fixed position relative to the plate 23 of the frame 1. In this fixed position, the longitudinal axis of the support plate 41 passes through the pivotal axle 22 and coincides with the axis OX of a fixed reference system OXYZ, in which the axis OZ coincides with the longitudinal axis of the shaft 11 of the plate 2 when the support plate 14 is in its fixed position, as shown in FIG. 5.

Then, for example in response to the depression of a button for starting the balancing cycle (not shown), the monitoring and control unit 27 activates the motor 16 to cause the plate 2 to turn at a predetermined speed of rotation, for example at a speed of about 300 rpm. At the same time, the unit 27 activates the electromagnet 26 so as to bring the indexing means 32 into their inactive position, in which the support plate 14 can pivot freely about the axle 22.

If the plate 8 has not been loaded in a uniform manner, there will be seen on this an unbalance B (FIG. 5), of which it is necessary to determine the angular position and the mass so that the unbalance can be compensated by at least one balancing mass so as to balance the plate 2. During rotation of the plate 2, the unbalance B is subject to a centrifugal acceleration $\vec{\gamma}_c$, whose component along the axis OY has a value given by the formula:

$$\gamma_c = \omega^2 \cdot r \cdot \sin(\omega t) \tag{1}$$

In which $\omega$ is the propulsion which is equal to $2\Pi f$, f being the speed of rotation of the plate 2 expressed in Hertz or turns per second, t is the time in seconds and r is the radius of gyration of the unbalance B, expressed in meters. For a given centrifuge, the radius r corresponds to the radius of the plate 2 and is thus known, as is the speed of rotation f. The values f and r can be stored in a memory of the monitoring and control unit 27. The centrifugal acceleration $\vec{\gamma}_c$, gives rise to a force $F_c$, whose component along the OY axis has a value which is given by the formula:

$$F_c = m_0 \cdot \gamma_c = m_0 \cdot \omega^2 \cdot r \cdot \sin(\omega t) \tag{2}$$

In which $m_0$ is the unknown mass of the unbalance B. The force $F_c$ is transmitted to the support plate 14 and to the assembly of the pieces carried by said plate (plate 2, basin 8, bearings 12 and 13, columns—crosspieces 15, motor 16, toothed pulleys 17 and 19, toothed belt 18, position detector 26 and acceleration detector 29) whose total mass M relative to the center of plate 2 is known from its construction. The value of the mass M can thus be stored in a memory of the monitoring and control unit 27. By designating with $\Gamma_0$ the component along the OY axis of acceleration to which the mass M is subject relative to the center of the plate, there can then be written:

$$F_c = M \cdot \Gamma_0 \tag{3}$$

From formulas (2) and (3), it can be deduced that:

$$F_c = M \cdot \Gamma_0 = m_0 \cdot \omega^2 \cdot r \cdot \sin(\omega t) \tag{4}$$

The component along the OY axis of the force $F_c$ thus has the effect of causing the support plate 14 to oscillate and, with it, the acceleration detector 29 on opposite sides of the axis OX, about the vertical axis 22, as indicated by the double arrow 71 in FIG. 5. An arcuate window 23a, centered on the axle 22, is provided in the plate 23 to permit clearance of the motor 16 when the plate 14 oscillates.

Figure 6:
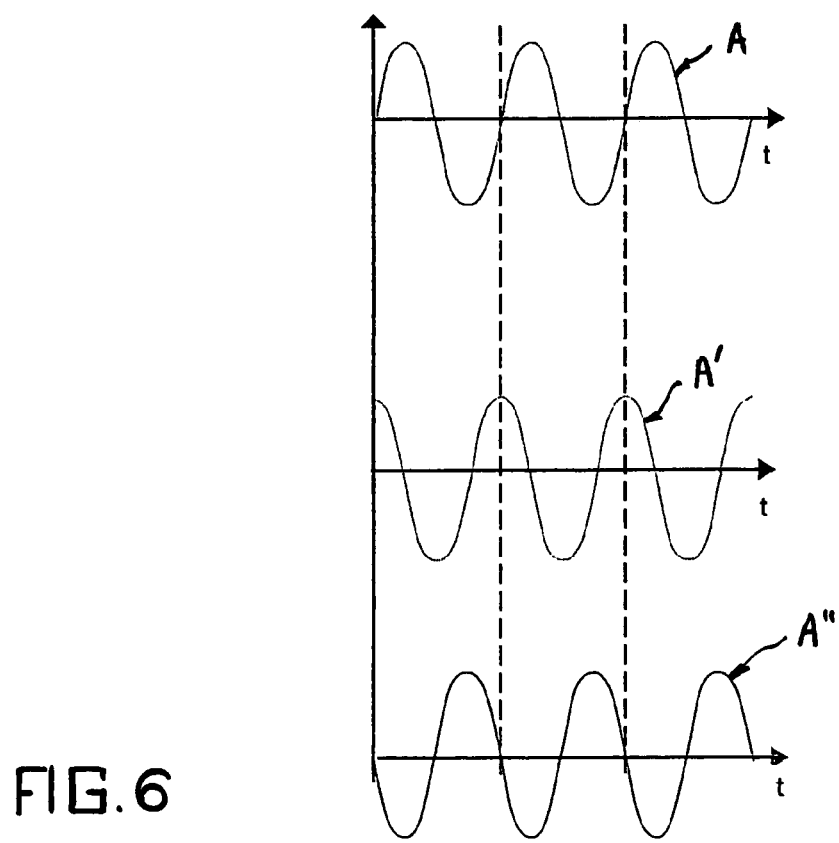
FIG. 6 is a graph of the movement of an oscillating support carrying the rotatable plate of the centrifuge.

On the graph of FIG. 6, the diagram A represents the movement of the acceleration detector 29 as a function of time, the diagram A' represents the speed of the acceleration detector 29 as a function of time and the diagram A" represents the acceleration of the acceleration detector as a function of time and also represents the waveform of the signal transmitted by said acceleration detector over the line 31 to the monitoring and control unit 27. This signal has a waveform which is in phase opposition to that of the movement represented by the diagram A. Its value is maximum when the amplitude of the movement is maximum along the axis OY, which is to say when $(\omega \cdot t) = (\Pi/2)$, namely when sin(ω·t)=1. This situation takes place when the unbalance B passes into a position corresponding with the axis OY in the course of the rotation of plate 2. To determine the angular position of the unbalance B on the plate 2, the monitoring and control unit 27 thus records the instantaneous value of the signal provided by the position detector 26 at the moment at which the value of the acceleration signal provided by the position detector 29, after analog/digital conversion in the monitoring and control unit 27, reaches its maximum value.

Figure 7:
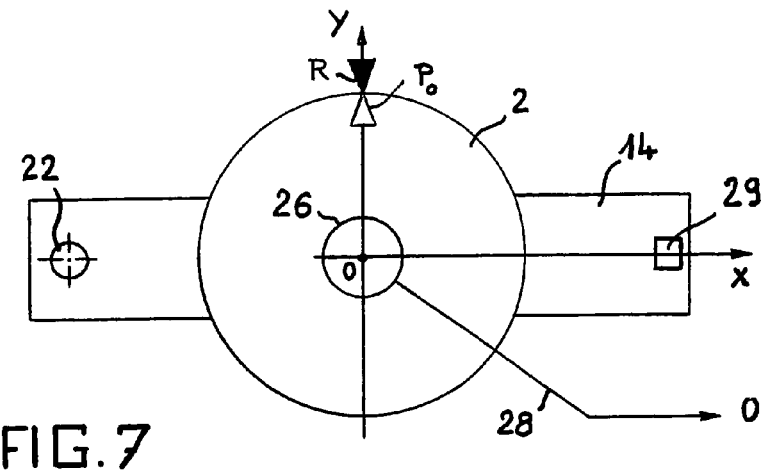
FIGS. 7 to 9 are schematic plan views similar to FIG. 5, showing the operation of a position detector used in the centrifuge to determine the angular position of an unbalance on the rotatable plate.
Figure 8:
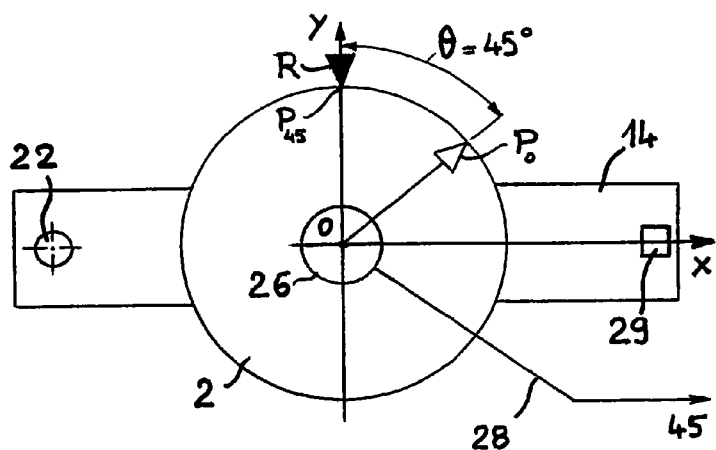

More precisely, the position detector 26 is preferably a detector of the absolute type. The angular position of its rotor, and as a result, the angular position of the plate 2 which is connected to the rotor of the position detector 26, is referenced relative to a fixed point designated by the reference character R in FIGS. 7, 8, 9 and 11. This fixed point is selected arbitrarily as the origin for the measurement of the angles and, in the example shown here, this point is located along the OY axis. The position detector 26 divides the circumference of the rotor, hence of the plate 2, into a certain number of points, for example 360 points designated by $P_0$ to $P_{359}$ in the clockwise direction, thereby giving a resolution of 1°/point. Of course, if it is desired to obtain greater resolution, there can be used a position detector dividing the circumference of the plate 2 into a larger number of points. Thus, in the example shown here, when the point $P_0$ of the plate 2 is located in correspondence with the reference mark R, the position detector 26 provides over the line 28 a signal having a value 0 as shown in FIG. 7. When the plate 2 has turned through an angle θ of for example 45° as shown in FIG. 8, the angular detector 26 delivers on the line 28 a signal having a value of 45 corresponding to the value of angle θ. Thus, all of the angle values transmitted by the position detector 26 over the line 28 to the monitoring and control unit 27 correspond to the angular distance between the fixed point R and the point $P_0$ on the plate 2, which is movable with this latter.

Figure 9:
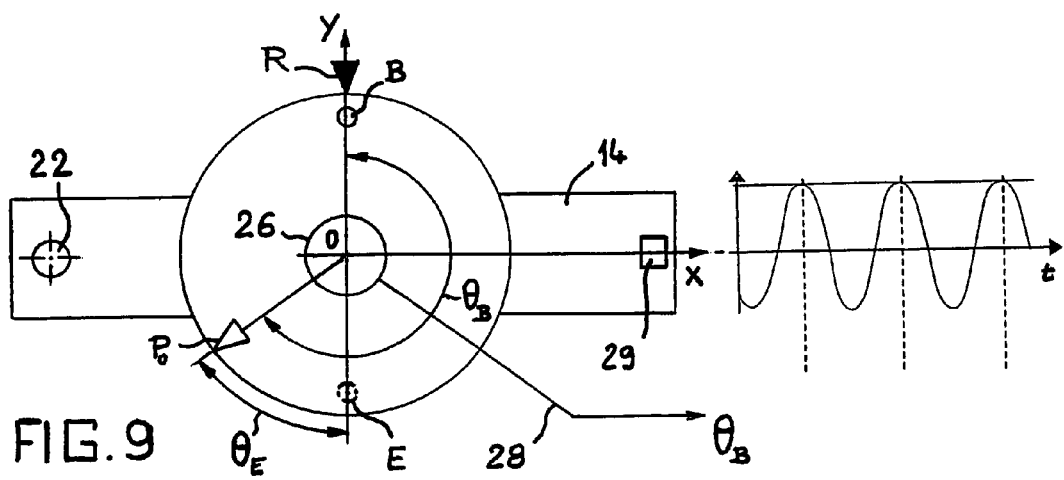

From the above, it will be seen that if the monitoring and control unit 27 records in its memory the value which is present in the line 27 at the moment at which the acceleration signal supplied by the acceleration detector 27 reaches a maximum value, which is to say when the unbalance B occupies a position in correspondence with the OY axis, the monitoring and control unit 27 will thus determine the angular distance of the unbalance B as being the angle $θ_B$ whose value is present at this moment in the line 28, as shown in FIG. 9. Then, by subtracting 180° from the recorded value $θ_B$, the calculating means included in the monitoring and control unit 27 determine the angular spacing $θ_E$ between the position $P_0$ of the plate 2 and the position of the point E which is diametrically opposed to the unbalance B and which is adapted to receive a balancing weight corresponding to the mass $m_0$ of the unbalance B.

If there is designated by $Γ'_0$ the value of acceleration measured by the monitoring and control unit (27) after analog/digital conversion of the signal from the acceleration detector (29), $Γ'_0$ is related to $Γ_0$ by the formula:

$$Γ'_0 = K·Γ_0 \qquad (5)$$

In which K is a coefficient of amplification which is equal to $L_2/L_1$. Thus, as is particularly shown in FIG. 5, the acceleration detector 29 is disposed on the support plate 14 in a position which is aligned with the center of the plate 2 and with the geometric center 72 of the pivotal axle 22, and which is preferably located at a distance $L_2$ from the center 72 which is greater than the distance $L_1$ from the center of the plate 2 to the center 72. This arrangement offers the following advantages: it permits mechanically amplifying, in the ratio $L_2/L_1$, the movement, speed and acceleration of the acceleration detector 27 relative to the movement, speed and acceleration of the center of the plate 2, hence to make the measurements at a lower speed than the speed of rotation corresponding to the nominal speed of centrifugation; in its turn, this permits limiting the angular movement of the plate 2 and of the support plate 14 about the axle 22 to a low value (about ±5°) and, as a result, to consider their small angular displacement at the level of the center of the plate 2 as being linear along the OY axis. Finally, this permits avoiding mechanical damages which otherwise could take place during measurements, which is to say at a time at which the unbalance can be great or has not yet been compensated, if the speed of rotation were high, or even near the nominal speed of centrifugation.

The value $Γ'_0$ of acceleration is itself also a maximum when the amplitude of movement of the acceleration detector 29 is maximum along the OY axis, which is to say when the unbalance B occupies the position shown in FIG. 9, facing the mark R. The monitoring and control unit 27 registers in its memory the maximum value of $Γ'_0$.

According to formulas (2), (3) and (5), there can be deduced the value of the mass $m_0$ as being equal to:

$$m_0 = \frac{Γ'_0}{γ_c} · \frac{M}{K} \qquad (6)$$

According to formula (6), it will be seen that the computing means included in the monitoring and control unit 27 can easily compute the value of the mass $m_0$ of the unbalance B based on the value of acceleration $Γ'_0$ measured by the acceleration detector 29 and from construction data M and K which are stored in the memory of said unit 27, and from the centrifugal acceleration $γ_c$. The value of $γ_c$ can be stored in said memory, or else calculated according to formula (1), from the value of the radius of gyration r, which is stored in said memory, and from the value of the pulsation ω corresponding to the predetermined speed of rotation for the determination of the unbalance (for example 300 rpm) which is itself also stored in said memory or calculable from a speed signal provided by a tachometer (not shown).

The position of the point E which is diametrically opposite the unbalance B on the plate 2 and which is adapted to receive a balancing weight, and the mass $m_0$ of the unbalance to be compensated having been determined in the manner described above, the balancing of the plate 2 can then be carried out by placing at the point E a balancing mass $m_1$ such that $m_1=m_0$. The balancing mass $m_1$ can be disposed in the form of a suitable quantity of liquid in at least one balancing container 6 with the help of the supplied device 21 described above. To do this, the monitoring and control unit 27 verifies whether the angular position determined for the point E corresponds to one of the defined known angular positions of the balancing containers 6, which are stored in the memory of said unit 27. If the result of this verification is positive, the unit 27 adopts as the angular position for the balancing mass, the angular position which was determined for the point E, but if not, it adopts the angular position of the balancing container which is nearest said angular position determined for the point E. As a modification, the unit 27 can adopt as the angular position for the balancing mass at least two angular positions corresponding to at least two balancing containers 6 which are located on opposite sides of the determined angular position for the point E.

The unit 27 also verifies whether the value of the mass $m_0$ of the unbalance, hence the value of the balancing mass $m_1$, is less than or equal to a maximum permissible mass of liquid in a balancing container 6. If the result of this second verification is positive and if the result of the first verification is itself positive, the unit 27 will then control the motor 16 to cause the plate 2 to turn at a reduced speed to bring the appropriate balancing container 6 to the fixed station at which the supply device 21 is located, so as to fill said appropriate balancing container with a mass of liquid $m_1$ equal to the previously calculated mass $m_0$ of the unbalance B. If the result of the second verification is negative, which is to say if the calculated mass $m_0$ is greater than the maximum admissible mass of liquid for a balancing container, the unit 27 will divide the value of the balancing mass $m_1$ into at least two balancing masses each having a value less than the maximum admissible mass of liquid, and the unit 27 will moreover adopt as its angular position for the at least two balancing masses, at least two angular positions corresponding to at least two balancing containers having defined positions located on opposite sides of the angular position determined for the point E. In this latter case, the values of the balancing masses corresponding to the fractions of the determined mass $m_0$ of the unbalance B and the positions for said balancing masses are calculated by the unit 27 such that the vectorial sum of the centrifugal forces due to said calculated balancing masses, once placed in the balancing containers located in the adopted angular positions, balances the centrifugal force due to the mass $m_0$ of the unbalance B.

The order in which are carried out the two above-mentioned verifications is not important. The unit 27 could thus, without departing from the scope of the invention, verify first of all the calculated value of the mass $m_0$ of the unbalance B, hence the value of the balancing mass $m_1$, is less than or equal to the maximum admissible mass of liquid for a balancing container, and then verify whether the angular position determined for the point E corresponds to one of the defined angular positions of the balancing containers 6.

In the case in which at least two balancing containers 6 must be filled with determined masses of liquid to balance the mass $m_0$ of the unbalance B, the control unit 27 actuates the motor 16 so as to bring the appropriate balancing containers 6 at reduced speed successively to the fixed station in which the supply device 21 is located, so as to fill one after the other the appropriate balancing container 6, respectively with appropriate quantities of liquid calculated by the unit 27.

Figure 11:
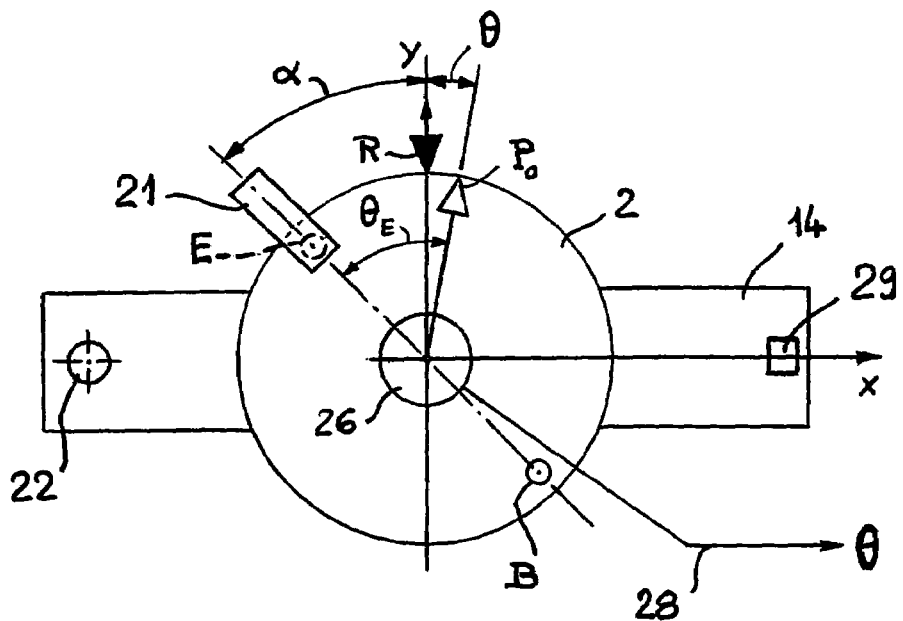
FIG. 11 is a schematic plan view similar to FIGS. 5, 7–9, permitting explaining how to bring a predetermined point of the rotatable plate of the centrifuge to a filling station so as there to load a balancing weight.

To bring the appropriate balancing container 6 into correspondence with the supply device 21, the unit 27 uses the signal supplied by the position detector 26 in the following manner. To put it simply, let it be supposed that in the determined angular position for the point E there is effectively a balancing container 6 and that the balancing container corresponding to the point E must be brought into registry with the supply device 21 as shown in FIG. 11. If there is designated by $\alpha$ the angular spacing between the fixed position corresponding to the mark R and the fixed position corresponding to the supply device 21, and if there is designated by $\theta$ the angular position of the plate 2 located facing the mark R when the point E occupies the sought position relative to the supply device 21, which is to say a position facing this latter, it will be seen from FIG. 11 that the angular spacing $\theta_E$ between the angular position $P_0$ and the angular position of the point E on the plate 2 is given by:

$$\theta_E = \alpha + \theta \tag{7}$$

However, according to FIG. 9, it will be seen that the angular spacing $\theta_E$ calculated by the unit 27 based on the angular position $\theta_B$ which has been determined for the unbalance B, the angle of spacing $\theta_E$ is also given by the formula:

$$\theta_E = \theta_B - 180° \tag{8}$$

According to formulas (7) and (8), it will be seen that the value of angle $\theta$ corresponding to the angular position of the plate (2) which must be located facing the mark R when the point E occupies the sought position facing the supply device 21, hence the value of the signal delivered at this moment by the position detector 26 along the line 28, is given by the formula:

$$\theta = \theta_B - 180° - \alpha \tag{9}$$

For example, if, by construction, the angle $\alpha$ is equal to 45° and if the value of the angle $\theta_B$ recorded in the memory of the unit 27 during determination of the position of the unbalance B is equal to 235° (FIG. 9), the value of the angle $\theta$ is thus equal to 10°, modulo 360° (a correction is thus necessary if, in the above example in which $\alpha$ is equal to 45°, the value of $\theta_B$ is in the range of [0°, 225°], terminals included).

To bring the point E into correspondence with the supply device 21, the monitoring and control unit 27 must thus cause the plate 2 to turn at a reduced speed and stop the latter at the time at which the signal provided by the position detector 26 along the line 28 is equal to the angle $\theta$, namely 10° in the numerical example above.

The process described above to determine the mass $m_0$ of the unbalance B, hence the balancing mass $m_1$ to be placed at the point E which is diametrically opposite the unbalance B on the plate 2, nevertheless supposes an approximation, namely that the mass of the specimens contained in the tubes 4 installed in the tube carrier 3 is negligible relative to the mass of the plate 2, of the support plate 14, of the motor 16 and of the other pieces of the centrifuge carried by the support plate 14. Thus, the mass of the specimen is not in principle known and the value of the mass M stored in the memory of the unit 27 corresponds only to the total mass of the support plate 14 and of all the pieces of the centrifuge carried by said plate 14. If it is desired to obtain even greater precision, there must be provided on the centrifuge or alongside the latter an electronic weighing device permitting weighing the specimen tubes, each filled with a specimen, before they are placed in the tube carriers 3 of the plate 2, and the value of the weight thus obtained can be introduced into the memory of the unit 27, for example by manual inclusion by means of a keyboard or by direct transfer from the weighing device, so as then to be added to the mass M.

However, in another embodiment of the process according to the invention, the balancing processes can be carried out in two phases. In a first phase, the mass $m_0$ of the unbalance B and the angular position of this latter are determined in the manner described above and a balancing $m_1$ is placed in the balancing container or containers corresponding to the position or positions determined by the unit 27 for the balancing mass or masses (for example at the point E). Then, the plate 2 is again rotated at the predetermined speed of rotation for the balancing process and if the compensation carried out during the first phase is not sufficient, which is to say if, after the first compensation for the mass $m_1$, there appears a new unbalance and that the latter is even more great relative to a range of tolerance defined in advance and placed in the memory of the unit 27, a second balancing phase is then automatically started. This second balancing phase takes account of the results acquired during the first phase. It is thus possible then to make a compensation which does not require an approximation in the calculations.

If a new unbalance appears after compensation by the balancing mass $m_1$, the support plate 14 is subjected to a new sinusoidal movement along the OY axis, which is caused by the combination of the two centrifugal forces due to the mass $m_0$ of the original unbalance B and the balancing mass $m_1$, and which obeys the equation:

$$\overline{(M+m_1)\cdot \Gamma_1} = \overline{m_0 \cdot \gamma_c \cdot \sin(\omega t)} + \overline{m_1 \cdot \gamma_c \cdot \sin(\omega t)} \quad (10)$$

in which $\Gamma_1$ is the acceleration relative to the center of plate 2 and which is undergone by the assembly comprising the support plate 14 and all the pieces carried by said plate, including the specimen tubes and the balancing mass $m_1$. The acceleration $\Gamma_1$ is measured by means of the acceleration detector 29 and, in the same way as for the first balancing phase, the new value $\Gamma'_1$ provided by the acceleration detector 29 is recorded in the memory of the monitoring and control unit 27 when $\omega t = \Pi/2$, namely when $\sin(\omega t) = 1$. It will be noted here that $\Gamma_1$ and $\Gamma'_1$ are connected by a relationship similar to that of equation (5), namely:

$$\Gamma'_1 = K \cdot \Gamma_1 \quad (11)$$

The vectors $\overrightarrow{m_0 \cdot \gamma_c}$ and $\overrightarrow{m_1 \cdot \gamma_c}$ being in opposite directions because the masses $m_0$ and $m_1$ are located in diametrically opposed positions on the plate 2, the modules of these two vectors have opposite sides. As a result, the equation (10) can again be written:

$$(M+m_1)\cdot \Gamma_1 = m_0 \cdot \gamma_c - m_1 \cdot \gamma_c \quad (12)$$

By replacing $\Gamma_1$ by its value drawn from equation (11) and by replacing M by its value drawn from equation (6), equation (12) becomes:

$$\left(K \cdot m_0 \cdot \frac{\gamma_c}{\Gamma'_0} + m_1\right)\frac{\Gamma'_1}{K} = m_0 \cdot \gamma_c - m_1 \cdot \gamma_c \quad (13)$$

From equation (13), the value of $m_0$ can be derived:

$$m_0 = \frac{m_1}{K} \cdot \frac{\Gamma'_0}{\gamma_c} \cdot \frac{K\gamma_c + \Gamma'_1}{\Gamma'_0 - \Gamma'_1} \quad (14)$$

As the values of $m_1$, K, $\Gamma'_0$, $\Gamma'_1$ and $\gamma_c$ have been previously recorded in the memory of the monitoring and control unit 27 and are thus known, said unit 27 can thus now calculate the real value of the mass $m_0$ of the initial unbalance B and, as a result, compute also the supplemental mass $m_2 = m_0 - m_1$ if a balancing mass $m_1$ should be previously placed on the plate 2 so as completely to balance the latter.

It follows that the embodiments of the invention that have been described above have been given purely by way of indicative example and are in no way limiting, and that numerous modifications can be resorted to by those skilled in the art without thereby departing from the scope of the invention.

The invention claimed is:

1. Process for balancing a rotating plate (2) of a centrifuge comprising a position detector (26) adapted to provide a signal indicative of an angular position of the rotating plate, and several tube carriers (3) which are located in predetermined angular positions at the periphery of the rotating plate and which each have means adapted to receive a specimen tube (4), characterized in that it comprises the steps consisting:
   a) in using as tube carriers, tube carriers (3) each having a balancing container (6) in addition to said means adapted to receive a specimen tube;
   b) in loading at least a certain number of said specimen tubes (3) each with a specimen tube (4) filled with a liquid specimen to be centrifuged;
   c) in turning the rotating plate (2) at a predetermined speed of rotation;
   d) in determining, based on said predetermined speed of rotation and on the basis of the signal provided by the position detector (26) and by a signal provided by the acceleration detector (29) coupled to the rotating plate (2), an angular position ($\theta_B$) and a mass ($m_0$) of an unbalance (B) on the rotating plate (2), due to unequal loading of said rotating plate;
   e) in determining, based on the angular position ($\theta_B$) of the unbalance (B) determined in step d), at least one angular position ($\theta_E$) on the rotating plate (2) or at least one balancing mass ($m_1$);
   f) in reducing the speed of the rotating plate (2) and in bringing it by slow rotation to a stop position such that the angular position determined in step e) will be located in correspondence with a fixed station (21) for the supply of a balancing product; and
   g) in filling the one of the balancing containers (6) which is located in the fixed supply station when the rotating plate is in said stop position, with a quantity of balancing product having a mass equal at least to a fraction of the mass ($m_0$) of the unbalance (B) determined in step d).

2. Process according to claim 1, characterized in that step e) consists:
   e1) in calculating the angular position which is diametrically opposite, on the rotating plate (2), to the angular position of the unbalance (B) determined in step d);
   e2) in verifying whether the angular position calculated in step e1) corresponds to one of said predetermined angular positions of the tube carriers (3) and of the balancing container (6) associated therewith and, in the affirmative, in adopting as the angular position for the balancing mass ($m_1$) the angular position calculated in step e1), and if not, in adopting as the angular position for the balancing mass ($m_1$) the angular position of the tube carrier and of the balancing container (6) associated therewith which is the nearest the angular position calculated in step e1).

3. Process according to claim 1, characterized in that step e) consists:
   e1) if calculating the angular position which is diametrically opposite, on the rotating plate (2), to the angular position of the unbalance (B) determined in step d);
   e2) in verifying whether the angular position calculated in step e1) corresponds to one of said predetermined angular positions of the tube carriers (3) and of the balancing container (6) associated therewith and, in the affirmative, in adopting as the angular position for the balancing mass ($m_1$) the angular position calculated in step e1), and if not, in adopting as angular positions for at least two balancing masses at least two angular positions corresponding to at least two of the tube carriers (3) and to the balancing containers (6) associated therewith which are located on opposite sides of the angular position calculated in step e1), and in calculating at least two balancing masses to be placed respectively in the balancing containers corresponding to the adopted angular positions, said calculated balancing masses corresponding to fractions of the mass of the unbalance determined in step d) such that the vectorial sum of the centrifugal forces due to the calculated balancing masses once placed in the balancing containers located in said adopted angular positions, balances the centrifugal force due to the mass of the unbalance.

4. Centrifuge comprising:
a) a frame (1)
b) a plate (2) mounted rotatably on the frame and having several tube carriers (3) located in predetermined angular positions along the periphery of the rotating plate, each tube carrier being adapted to receive a specimen tube (4);
c) drive means (16–19) to turn the rotating plate;
d) a position detector (26) adapted to provide a signal indicative of an angular position of the rotating plate;
e) a monitoring and control unit (27) receiving said signal indicative of the angular position and adapted to control said drive means (16–19) so as to cause the rotating plate to turn (2) at at least one predetermined speed of rotation and to stop said rotating plate in predetermined angular positions;
characterized by
f) several balancing containers (6) which are respectively associated with tube carriers (3) on the rotating plate (2);
g) an acceleration detector (29) adapted to provide a signal indicative of the value of the centrifugal acceleration to which the rotating plate (2) is subjected when it turns at a predetermined speed;
h) a device (21) for supplying a balancing product located on the frame (1) at a station adjacent to the periphery of the rotating plate (2);
i) calculating means included in the monitoring and control unit (27), adapted to determine, on the basis of said predetermined speed of rotation and on the basis of the signals provided by the position detector and the acceleration detector, an angular position ($\theta_B$) and a mass ($m_0$) of an unbalance (B) on the rotating plate (2), due to unequal loading of said rotating plate;
j) said calculating means being adapted to determine, on the basis of the determined angular position ($\theta_B$) of the unbalance (B), at least one angular position ($\theta_E$) on the rotating plate (2) for at least one balancing mass ($m_1$);
k) said monitoring and control unit (27) being adapted to control said drive means (16–19) such that the latter bring the rotating plate (2) into a stop position such that the angular position determined for the balancing mass ($m_1$) is located in correspondence with said fixed station, and in controlling said device (21) for supplying a balancing product to fill the one of the balancing containers (6) which is located at the fixed station when the rotating plate (2) is in said stop position, with a quantity of balancing product having a mass equaled to at least a fraction of the mass ($m_0$) of the unbalance (B) determined by the calculating means.

5. Centrifuge according to claim 4, characterized in that said rotating plate (2), said position detector (26), said acceleration detector (29) and said drive means (16–19) are carried by a movable support (14) which is pivotally mounted relative to the frame (1) about a vertical pivotal axle (22) parallel to the axis of rotation (11) of the rotating plate and which is adapted to swing to opposite sides of a neutral position when the rotating plate turns at said predetermined speed with an unequal load.

6. Centrifuge according to claim 5, characterized in that the axis of rotation (11) of the rotating plate (2) is located at a first distance (L1) from the vertical pivotal axle (22), and the acceleration detector is located at a second distance (L2) from said vertical pivotal axle (22) in a vertical plane defined by said vertical pivotal axle and by said axis of rotation, said second distance (L2) being greater than said first distance (L1).

7. Centrifuge according to claim 6, characterized in that said calculating means calculate the mass ($m_0$) of the unbalance (B) according to a first formula:

$$m_0 = \frac{\Gamma'_0}{\gamma_c} \cdot \frac{M}{K}$$

in which $\Gamma'_0$ is a value of acceleration measured by the acceleration detector (29), K is a coefficient of amplification whose value is equal to the ratio (L2/L1) of said second and first distances, M is the total mass of the movable support (14) and of all the pieces of the centrifuge carried by said movable support; and $\gamma_c$ is the value of centrifugal acceleration due to the mass $m_0$ of the unbalance (B) when the rotating plate (2) turns at the predetermined speed of rotation.

8. Centrifuge according to claim 7, characterized in that the calculating means recalculate the mass $m_0$ of the unbalance (B) according to a second formula:

$$m_0 = \frac{m_1}{K} \cdot \frac{\Gamma'_0}{\gamma_c} \cdot \frac{\Gamma'_1 + K\gamma_c}{\Gamma'_0 - \Gamma'_1}$$

in which $m_1$ is a first balancing mass calculated according to the first formula and $\Gamma'_1$ is a value of acceleration measured by the acceleration detector (29) when the rotating plate (2) provided with the first balancing mass is driven in rotation at the predetermined speed of rotation, and the calculating means then calculate a second balancing mass $m_2 = m_0 - m_1$, from the second formula so as to complete the balancing of the rotating plate.

9. Centrifuge according to claim 5, characterized in that it comprises disengageable indexing means (32) which are controlled by the monitoring and control unit (27) so as to maintain said movable support (14) in said neutral position when the rotating plate (2) is stopped and when it turns at a speed substantially slower than said predetermined speed of rotation.

10. Centrifuge according to claim 4, characterized in that the balancing product is a liquid (69).

11. Centrifuge according to claim 10, characterized in that the device (21) for supplying balancing product comprises
a) at fixed station, a vertical hollow needle for filling and emptying (41) and a mechanism for raising and lowering (61), controlled by the monitoring and control unit (27), to move vertically said needle (41) between an upper ready position, in which the lower end of the needle is at a higher level than an upper opening of the balancing container (6) to be filled, and at least one lower filling/emptying position in which said needle (41) is engaged in said balancing container (6) to be filled or emptied;
b) a reservoir (42) for balancing liquid; and
c) a pump (43) connected to said reservoir (42) of balancing liquid and to said needle (41) by flexible tubes (44–48) and by an electrovalve (49) controlled by the monitoring and control unit (27), said electrovalve having a neutral ready position, a first working position in which the balancing liquid can circulate from the reservoir (42) toward the needle (41), and a second working position in which the balancing liquid can circulate from the needle (41) toward the reservoir (42).

12. Centrifuge according to claim 11, characterized in that it moreover comprises a liquid level detector (63) arranged to detect a liquid level in the balancing container (6) located at said fixed station and to provide a signal indicative of the detected liquid level usable by the monitoring and control unit (27) to control the pump (43) and/or the electrovalve (49).

\* \* \* \* \*